United States Patent [19]

Borror et al.

[11] Patent Number: 4,615,966
[45] Date of Patent: Oct. 7, 1986

[54] COLOR TRANSFER PHOTOGRAPHIC PROCESSES AND PRODUCTS WITH INDOLE PHTHALEIN FILTER DYES

[75] Inventors: Alan L. Borror, Andover; Efthimios Chinoporos, Belmont; Cheryl P. Petersen, Arlington, all of Mass.

[73] Assignee: Polaroid Corporation, Cambridge, Mass.

[21] Appl. No.: 821,074

[22] Filed: Jan. 21, 1986

Related U.S. Application Data

[63] Continuation-in-part of Ser. No. 752,444, Jul. 3, 1985, abandoned.

[51] Int. Cl.⁴ .................. G03C 1/40; G03C 1/84; G03C 5/54; C07D 405/00
[52] U.S. Cl. .................. 430/221; 430/227; 430/236; 430/244; 430/449; 430/517; 548/456
[58] Field of Search .............. 430/221, 517, 236, 227, 430/244, 449; 548/456

[56] References Cited

U.S. PATENT DOCUMENTS

| | | | |
|---|---|---|---|
| 3,415,644 | 12/1968 | Land | 430/212 |
| 3,415,645 | 12/1968 | Land | 430/212 |
| 3,415,646 | 12/1968 | Land | 430/212 |
| 3,647,646 | 3/1972 | Land | 430/221 |
| 3,702,244 | 11/1972 | Bloom et al. | 430/221 |
| 3,702,245 | 11/1972 | Simon et al. | 430/221 |
| 4,456,674 | 6/1984 | Cerankowski et al. | 430/221 |

Primary Examiner—Richard L. Schilling

[57] ABSTRACT

This invention relates to diffusion transfer photographic processes adapted to be performed in the presence of ambient light and to diffusion transfer products useful in such processes wherein enhanced opacification particularly, in the green region of the visible spectrum is achieved by employing a 7-sulfonamido/5- or 6-sulfamoyl indole phthalein as the light-absorbing, pH-sensitive optical filter agent for the shorter wavelength region of the visible spectrum.

29 Claims, 3 Drawing Figures

COLOR TRANSFER PHOTOGRAPHIC PROCESSES AND PRODUCTS WITH INDOLE PHTHALEIN FILTER DYES

This application is a continuation-in-part of copending U.S. patent application Ser. No. 752,444 filed July 3, 1985, now abandoned.

BACKGROUND OF THE INVENTION

1. Field of the Invention

This invention relates to photography, and more particularly, it relates to photographic processes performed in ambient light and to photographic products useful in such processes.

2. Description of the Prior Art

A number of diffusion transfer processes for producing photographic images in both black-and-white and in color are now well known. Of particular interest are diffusion transfer processes wherein the image-receiving layer carrying the transfer image is not separated from the developed photosensitive layer(s) after processing but both components are retained together as a permanent laminate. Included as part of the laminate is a layer of a light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer. Diffusion transfer processes for forming images viewable without separation of the photosensitive and image-receiving components and film units useful in such processes are described, for example, in U.S. Pat. Nos. 3,415,644, 3,415,645 and 3,415,646 issued Dec. 10, 1968 to Edwin H. Land.

U.S. Pat. No. 3,647,437 issued Mar. 7, 1972 to Edwin H. Land also is concerned with diffusion transfer processes wherein the resulting photograph comprises the developed photosensitive layer(s) retained with the image-receiving layer as part of a permanent laminate. In the processes disclosed in this patent, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. In a particularly preferred embodiment, the film unit is of the type described in aforementioned U.S. Pat. No. 3,415,644 and comprises a first sheet-like component comprising an opaque support carrying a silver halide emulsion layer(s) and a second sheet-like component comprising a transparent support carrying an image-receiving layer which are in fixed relationship prior to exposure, which relationship is maintained after processing. After photoexposure through said transparent support, an aqueous alkaline processing composition is distributed in a thin layer between said components. The processing composition contains a light-reflecting pigment and at least one pH-sensitive dye which is in its colored form at the initial pH of said aqueous alkaline processing composition and which, after at least the initial stages of processing, is converted to its colorless form by reducing the environmental pH, for example by including an acid-reacting layer as part of the film unit. The concentrations of the light-reflecting pigment and light-absorbing optical filter agent required to provide adequate protection of the photosensitive layer(s) will vary with the process being performed and the anticipated conditions, e.g., light intensity, dark time etc. Preferably, the concentrations of these materials are such that the processing composition layer containing the pigment and optical filter agent will have a transmission density of at least about 6 but a reflection density not greater than about 1.

Various pH-sensitive dyes have been disclosed as light-absorbing optical filter agents for protecting a selectively exposed photosensitive material from post-exposure fogging in the presence of extraneous incident light. Examples of pH-sensitive dyes that have been found particularly useful are the phthaleins, i.e., the phthalide and naphthalide dyes derived from 1-naphthols disclosed in U.S. Pat. No. 3,702,245 issued Nov. 7, 1972 to Myron S. Simon and David P. Waller and the phthalide and naphthalide dyes derived from indoles disclosed in U.S. Pat. No. 3,702,244 issued Nov. 7, 1972 to Stanley M. Bloom, Alan L. Borror, Paul S. Huyffer and Paul T. MacGregor. As discussed in the latter patent, indole phthaleins especially useful for photographic processes employing highly alkaline media are those containing a 2-ortho-hydroxyphenylindol-3-yl radical and a second indol-3-yl radical substituted in the 7-position with, for example, carboxy, sulfonamido or sulfamoyl or a second indol-3-yl radical substituted in the 5-position with an electronwithdrawing group, for example, carboxy or cyano and indole phthaleins containing a 7-carboxy-indol-3-yl radical and a second indol-3-yl radical substituted in the 7-position with, for example, sulfonamido or sulfamoyl. As discussed in these and other patents, a combination of the indole and 1-naphthol phthaleins generally are used where it is desired to provide protection from post-exposure fogging throughout the visible spectrum.

U.S. Pat. No. 4,456,674 issued June 26, 1984 to Leon D. Cerankowski, Gary S. LaPointe and Neil C. Mattucci discloses enhanced opacification systems employing metal cations for complexing with the phthalein optical filter agents and in one embodiment discloses the use of certain bivalent transition metal cations, such as, zinc and cadmium for complexing with the carboxyindole phthalein to increase opacification in the green region of the visible spectrum (500–600 nm). Presumably, these bivalent metal cations bind with the indole nitrogen of the carboxyindole phthalein to produce a spectral shift in dye $\lambda_{max}$ from the mid-400 nm range to over 500 nm thereby increasing the transmission density of the pigmented processing composition layer in the spectral region where opacification failures first manifest themselves due to thin spots in reagent spreading or using lesser quantities of processing composition, i.e., thinner layers of reagent.

SUMMARY OF THE INVENTION

According to the present invention, it has now been found that certain 7-sulfonamido/sulfamoyl indole phthaleins, namely, 7-sulfonamido/6-sulfamoyl and 7-sulfonamido/5-sulfamoyl indole phthaleins, provide enhanced protection against post-exposure fogging in the green region of the visible spectrum. At the time parent application Ser. No. 752,444 was filed, it was mistakenly believed that the sulfamoyl group was substituted in the 7-position of the indolyl radical, that is, it was believed that the phthaleins were 7-sulfonamido/7-sulfamoyl indole phthaleins. Subsequently, it was found that the sulfamoyl group actually was substituted in the 6-position rather than in the 7-position of the indolyl radical and that the sulfamoyl-substituted indole intermediate used in the synthesis of the naphthalide dye product of the example was 6-methylsulfamoylindole. This inadvertent error in assigning the position of the methylsulfamoyl group was discovered as a result of the further characterization of the methylsulfamoylindole intermediate by nmr, mass spectroscopy and X-ray analysis. Also, it has been found that 7-sulfonamido/5-sulfamoyl indole phthaleins are similarly useful in providing protection from post-exposure fogging in the green region of the visible spectrum.

As compared to 7-substituted indole phthaleins, such as, 7-carboxy/7-sulfonamido indole phthalein and 7-sulfonamido/7-sulfamoyl indole phthalein, the 7-sulfonamido/6-sulfamoyl and 7-sulfonamido/5-sulfamoyl indole phthaleins of the present invention possess a broader absorption spectrum extending further into the green region of the visible spectrum and absorb incident radiation more strongly in the green region as evidenced by their higher epsilons. Because of these improved spectral absorption chracteristics, the subject indole phthalein optical filter agents allow the use of thinner layers of pigmented reagent and/or more efficient use, i.e., lesser concentrations of optical filter agent without requiring the addition of metal salts or other material to give added protection in the green region of the visible spectrum.

It is, therefore, the primary object of the present invention to provide diffusion transfer photographic products and processes employing as the processing composition, an aqueous alkaline solution of a light-reflecting pigment and a 7-sulfonamido/5-sulfamoyl or a 7-sulfonamido/6-sulfamoyl indole phthalein as at least one light-absorbing pH-sensitive optical filter agent.

It is another object of the present invention to provide photographic products and processes of the foregoing type wherein the processing composition additionally includes a light-absorbing, pH-sensitive carboxynaphthol phthalein optical filter agent.

It is a further object of the present invention to provide 7-sulfonamido/5-sulfamoyl indole phthaleins and 7-sulfonamido/6-sulfamoyl indole phthaleins useful as light-absorbing, pH-sensitive optical filter agents.

Other objects of this invention will in part be obvious and will in part appear hereinafter.

The invention accordingly comprises the processes involving the several steps and the relation and order of one or more of such steps with respect to each of the others, and the products possessing the features, properties and relation of elements which are exemplified in the following detailed disclosure, and the scope of the application of which will be indicated in the claims.

For a fuller understanding of the nature and objects of the invention, reference should be had to the following detailed description taken in conjunction of the accompanying drawings.

DETAILED DESCRIPTION OF THE INVENTION

Figure 1:
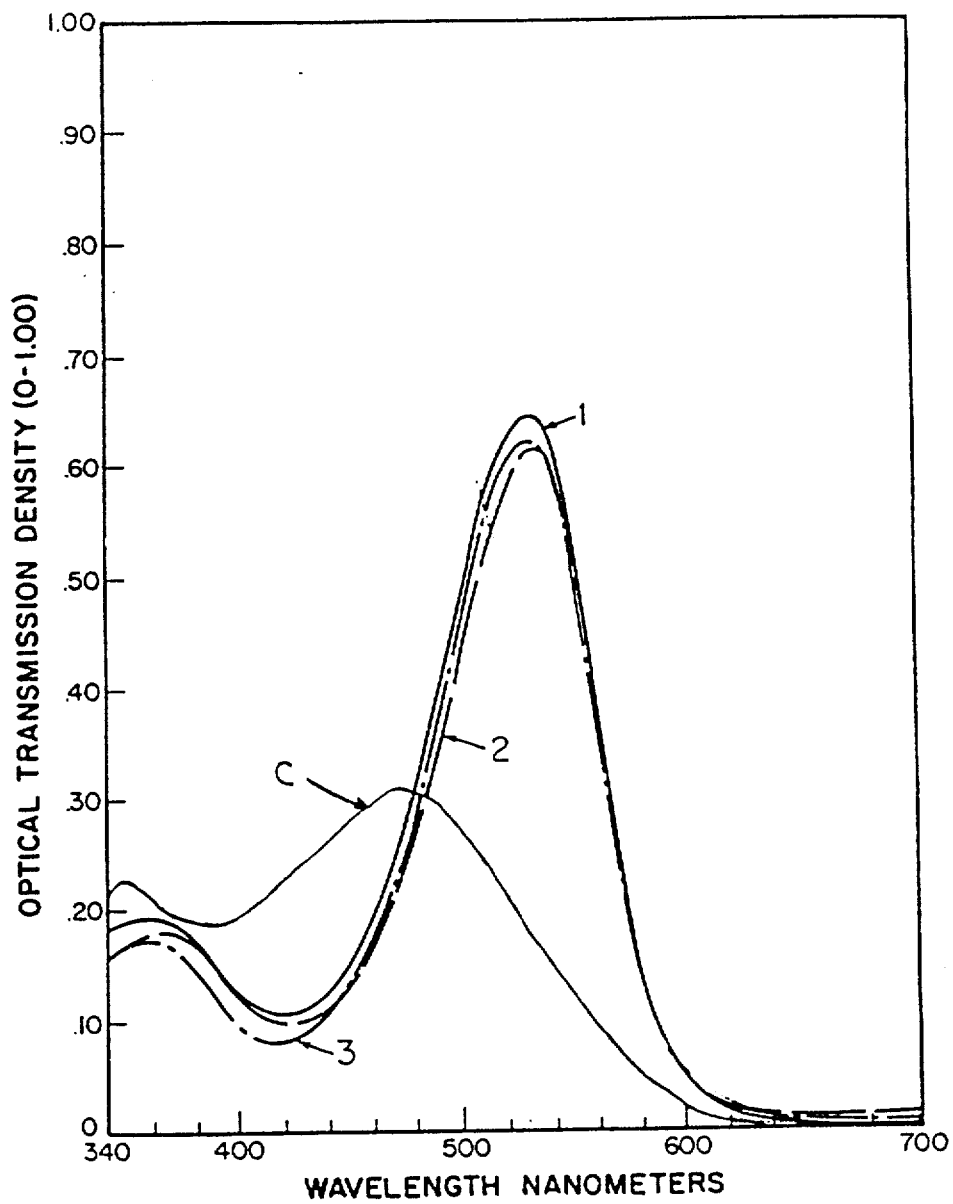
FIG. 1 is a graphic illustration comparing the spectral absorption characteristics of the indole phthalein optical filter agents of Examples 1, 2 and 3 of the present invention designated Curves 1, 2 and 3, respectively, with the spectral absorption characteristics of a 7-carboxy/7-sulfonamido indole phthalein optical filter agent (Curve C). These curves represent the optical transmission density, i.e., absorbance of the respective optical filter agents measured over the wavelength range of 340 nm to 700 nm in aqueous alkaline solution.

As noted above, it has been found that enhanced opacification of a pigmented processing composition layer and, particularly, added protection in the green region of the visible spectrum can be achieved by employing certain indole phthaleins as the light-absorbing, pH-sensitive optical filter agent for the shorter wavelength region of the visible spectrum. These indole phthaleins may be represented by the formula

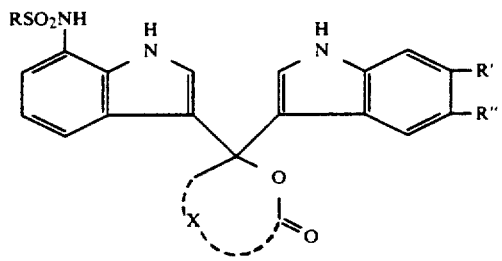

wherein R is selected from alkyl, aryl, aralkyl and alkaryl, R' and R" each are selected from hydrogen, halo and —$SO_2NR^1R^2$ provided one of said R' and R" is said —$SO_2NR^1R^2$, $R^1$ and $R^2$ each are selected from hydrogen, alkyl, aryl, aralkyl and alkaryl, and X represents the carbon atoms necessary to complete phthalide or naphthalide. The respective phthalide and naphthalide moieties are represented by the following formulae:

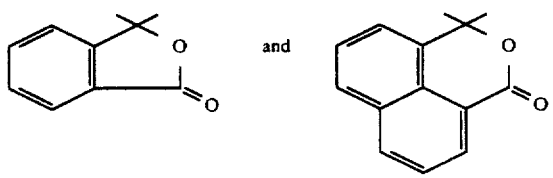

Preferably, X completes naphthalide.

Suitable R, $R^1$ and $R^2$ substituents include branched or straight chain alkyl usually containing 1 to 20 carbon atoms, e.g., methyl, ethyl, isopropyl, n-butyl, t-butyl, hexyl, octyl, dodecyl, hexadecyl, octadecyl and eicosanyl; aryl, e.g., phenyl and naphthyl; alkaryl, e.g., alkyl-substituted phenyl wherein the alkyl usually contains 1 to 20 carbon atoms, such as, p-methylphenyl and p-dodecylphenyl; and aralkyl, e.g., phenyl-substituted alkyl wherein the alkyl usually contains 1 to 20 carbon atoms, such as, benzyl, phenethyl and phenylhexyl. Where it is desired that the indole phthalein be relatively immobile in the processing composition layer, at least one of R, $R^1$ and $R^2$ comprises a long chain substituent, preferably, a long chain alkyl. When R' or R" is halo, it is usually bromo or chloro.

In addition to the named substituents, it will be appreciated that the subject compounds may be substituted with solubilizing groups, such as, carboxy, hydroxy or sulfonyl to enhance the solubility of the compound in the processing composition or substituted with additional immobilizing groups, such as, long chain alkoxy or alkyl or other groups as may be desired which do not interfere with its photographic function as an optical filter agent.

The subject indole phthaleins may be prepared using any of the various methods previously disclosed for synthesizing phthalides and naphthalides. A preferred method is described in U.S. Pat. No. 3,931,228 issued Jan. 6, 1976 to Alan L. Borror and comprises reacting a 7-sulfonamido (or 5- or 6-sulfamoyl) indole with phthalaldehydic or naphthaldehydic acid in the presence of a mild acid catalyst, e.g., toluene-p-sulfonic acid to yield the corresponding phthalidyl- or naphthalidylindole intermediate which is oxidized by treating with, for example, 2,3-dichloro-5,6-dicyano-1,4-benzoquinone. The oxidized intermediate is then reacted with a 5- or 6-sulfamoyl indole (or 7-sulfonamido indole) in the presence of an acid catalyst to yield the desired phthalein product. The 7-sulfonamido indoles employed in the above-described method are known and may be prepared according to the procedure disclosed in U.S. Pat. No. 3,772,329 issued Nov. 13, 1973 to Paul S. Huyffer. The procedure described therein for sulfamoyl-substituted indoles can be used for preparing 6-sulfamoyl indoles.

The following examples are given to illustrate the invention and are not intended to limit the scope thereof.

EXAMPLE 1

3-(7-n-hexadecylsulfonamidoindol-3-yl)-3-(6-methyl-sulfamoylindol-3-yl)naphthalide having the formula

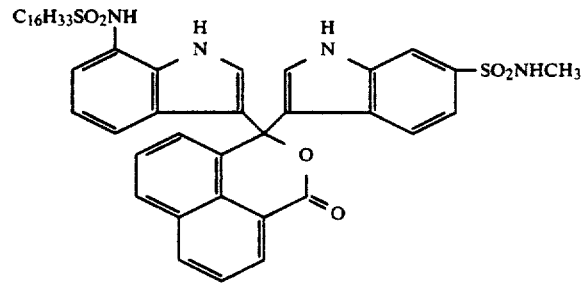

was prepared as follows:

(a) A mixture of naphthaldehydic acid (20 g., 0.0998 mol) and 7-hexadecylsulfonamidoindole (41.9 g., 0.0998 mol) were dissolved in 380 ml toluene and 61 ml acetic acid containing 0.3 g. of p-toluenesulfonic acid. This mixture was refluxed with a Dean-Stark trap for approximately 24 hours. At that time no more water was being removed and thin layer chromatography with chloroform showed the reaction was complete. The mixture was cooled and the solvents were removed under reduced pressure. The purple oil was dissolved in hot isopropanol and the crystals obtained were collected by suction filtration. After washing several times with ethanol until the wash became clear, 7.3 g. of naphthalidyl-indole intermediate was obtained.

This reaction was repeated using 0.175 mol each of naphthaldehydic acid and 7-hexadecylsulfonamidoindole to give 48.0 g. of the corresponding naphthalidylindole intermediate.

(b) To a stirred solution of the naphthalidylindole intermediate (1.0 g, 1.6 mmol) in 2 ml of dioxane was added 2,3-dichloro-5,6-dicyano-1,4-benzoquinone (0.45 g., 1.9 mmol). The resulting brown solution was refluxed for 30 minutes. At that time TLC using 5% methanol/methylene chloride showed no starting material. The cooled mixture was filtered and dioxane was removed under reduced pressure. The oxidized intermediate obtained was treated with ethanol/water.

This reaction was repeated using 20 g (0.033 mol) of naphthalidyl-indole intermediate and 9.04 g (0.039 mol) of 2,3-dichloro-5,6-dicyano-1,4-benzoquinone to give 19.55 g of the corresponding oxidized intermediate.

(c) To a stirred solution of the oxidized intermediate (16.58 g., 0.027 mol) and 100 ml of trifluoroacetic acid was added 6-methylsulfamoylindole (5.67 g., 0.0269 mol). The resulting solution was stirred at 25° C. After 36 hours, TLC using 12% methanol/chloroform showed the reaction to be complete. The reaction solution was added cautiously to a beaker of ice and filtered by suction filtration. It was washed several times with water and then dried in a vacuum oven at 75° C. for 12 hours. 20.47 g. of crude product was obtained. This was dissolved in chloroform, filtered through Celite and purified by high pressure liquid chromatography using two silica gel columns eluted with 3.8 liters of methylene chloride, 3.8 liters of 0.5% methanol/methylene chloride, 7.6 liters of 1.0% methanol/methylene chloride and 7.6 liters of 1.1% methanol/methylene chloride. 6.0 g of pure title compound was recovered as a tan crystalline compound.

The 6-methylsulfamoylindole employed above was prepared as follows:

To a 3-neck 500 ml round bottom flask containing 108.5 g (0.911 mol) indoline was added acetic anhydride at a rate such as to maintain a temperature below 25° C. After addition (one hour), the reddish sludge was poured into ice water, filtered and washed several times with water. It was allowed to dry overnight and recrystallized from 700 ml of ethanol and gave 116.6 g (72.4% by weight yield) of N-acetylindoline.

To N-acetylindoline, 116.6 g (0.724 mol) in a 1000 ml 3 neck flask fitted with overhead stirrer, thermometer and gas inlet (to a sodium hydroxide trap) in 150 ml acetic acid was added bromine, 32.25 ml (0.68 mol) over a period of 30 minutes. The mixture was kept at 30° C. with ice bath cooling. When addition was complete, the yellow suspension was slowly poured into one liter of ice water and solid sodium bisulfite was added to destroy any residual bromine. The resulting slightly off white solid was filtered and washed several times with water and allowed to dry overnight. The resulting solid was recrystallized from 800 ml of methanol to give 122.86 g (70.7% by weight yield) of 5-bromo-N-acetylindoline.

To 5-bromo-N-acetylindoline 122.86 g (0.51 mol) cooled in an ice bath was added chlorosulfonic acid, 116.52 g (2.6 moles) very cautiously. The mixture was stirred for about 30 minutes at 0° C. and then allowed to warm to room temperature. The mixture was then heated slowly to about 70°-90° C. overnight. After cooling, the cold solution was slowly added to ice and the solids collected by suction filtration, washed several times with water and allowed to dry overnight. The product was recrystallized from chloroform to give 72.5 g (42% by weight yield) of 5-bromo-6-chlorosulfonyl-N-acetylindoline.

To a suspension of 5-bromo-6-chlorosulfonyl-N-acetylindoline, 71.83 g (0.212 mol) in tetrahydrofuran was added a 40% aqueous solution of 2 equivalents of methylamine and 2 equivalents of triethylamine. The mixture was heated to reflux for 1.5 hours, then allowed to cool. Thin layer chromatography with chloroform showed that the reaction was complete. The cooled mixture was evaporated under reduced pressure, and the resulting white solid was suppended in hot methanol, filtered and washed with methanol and allowed to dry overnight. 65.12 g of 5-bromo-6-methylsulfamoyl-N-acetylindoline was obtained (92% by weight yield).

To a stirred suspension of 65.11 g (0.195 mol) of 5-bromo-6-methylsulfamoyl-N-acetylindoline in 200 ml dioxane was added 146 ml (1.75 mol) concentrated hydrochloric acid. The mixture was stirred and refluxed for 1.5 hours and allowed to cool. The mixture was then concentrated under reduced pressure, cooled in an ice bath and neutralized with 10% sodium hydroxide solution to pH 7. The resulting white precipitate was filtered, washed several times with water and allowed to dry overnight to give 55.92 g (98% by weight yield) of 5-bromo-6-methylsulfamoylindoline.

To a stirred solution of 5-bromo-6-methylsulfamoylindoline, 55.92 g (0.19 mol) in 150 ml dioxane was added 41.79 gm (0.184 mol) of 2,3-dichloro-5,6-dicyanobenzoquinone at 25° C. The resulting brown solution was heated to 80° C. for 2 hours when thin layer chromatography using chloroform showed that the reaction was complete. The reaction mixture was allowed to cool, filtered through Celite and the filtrate concentrated under reduced pressure. The resulting brown solid was stirred in a mixture of methylene chloride/ether 50/50 and then filtered. This procedure was carried out two additional times and gave 35.2 g (63.9% by weight yield) of 5-bromo-6-methylsulfamoylindole.

A solution of 8.68 g (0.299 mol) of 5-bromo-6-methylsulfamoylindole in ethanol was degassed under nitrogen for 15 minutes. Then triethylamine (0.036 mol) was added and then 1.09 g of palladium catalyst. The mixture was hydrogenated (40 psi) for 3 hours. Thin layer chromatography (2.5% methanol/methylene chloride) showed the reaction was complete. The mixture was filtered to remove the catalyst and then concentrated under reduced pressure. The oil remaining was taken up in chloroform and concentrated under reduced pressure four times to remove traces of ethanol solvent. The oil was chromatographed on a silica gel column eluted with 2.5% methanol/methylene chloride. The golden solution was concentrated under vacuum to give an oil. The oil was mixed with water and a tan solid precipitated. After cooling overnight, the tan solid was isolated by vacuum filtration and then washed with water. The solid was allowed to dry and then crushed to a powder which was allowed to further dry. 5.76 g (91.2% by weight yield) of 6-methylsulfamoylindole was obtained. M/e 210 $^1$H-NMR: (DMSO) δ7.859 (m,1H), 7.728 (d, 1H), 7.63 (t, 1H), 7.39 (dd,1H), 7.25 (q, 1H), 6.57 (t,1H), 2.37 (d,3H).

EXAMPLE 2

3-(7-n-hexadecylsulfonamidoindol-3-yl)-3-(5-methylsulfamoylindol-3-yl)naphthalide having the formula

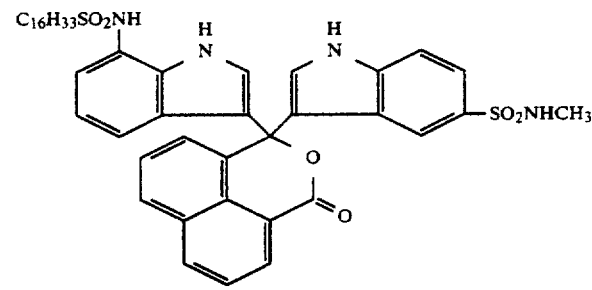

was prepared as follows:

(a) To a stirred solution of 4.32 g (0.0205 mol) of 5-methylsulfamoylindole in 200 ml of glacial acetic acid was added 4.104 g (0.0205 mol) of naphthaldehydic acid. The mixture was heated to reflux. 7 ml of p-toluenesulfonic acid was added to the reaction mixture. The solution was refluxed for 3 hours. Thin layer chromatography in 2% methanol/methylene chloride showed the reaction was complete. The solution was allowed to cool and then added to 2 liters of ice water. The tan solid was collected by suction filtration and allowed to air dry to give 6.854 g (0.0174 mol) (85% by weight yield) of naphthalidyl-indole intermediate.

(b) To a stirred solution of the naphthalidyl-indole intermediate, 5.965 g (0.015 mol) in 200 ml of dioxane was added 3.412 g (0.015 mol) of 2,3-dichloro-5,6-dicyano-1,4-benzoquinone. The mixture was refluxed for 6 hours. Thin layer chromatography in 3/1 ethylacetate/hexane showed the reaction was complete. The solution was allowed to cool, filtered through Celite and concentrated under reduced pressure. The dried residue was covered with chloroform and then dissolved in acetone. Hexane was added to the chloroform-acetone solution to precipitate the product. The pink solid was collected by suction filtration and was allowed to air dry to give 4.962 g (0.0127 mol) (85% by weight yield) of oxidized naphthalidyl-indole intermediate.

(c) To a stirred solution of 4.883 g (0.0125 mol) of oxidized intermediate in 100 ml of glacial acetic acid was added 5.25 g (0.0125 mol) of 7-n-hexadecylsulfonamidoindole. To the mixture was added 100 ml of trifluoroacetic acid. The reaction mixture was stirred at room temperature for 24 hours. Thin layer chromatography in 2% methanol/methylene chloride showed the reaction was complete. The solution was poured over 2 liters of ice water. The pink solid was collected by suction filtration and purified by high pressure liquid chromatography eluted with 1% methanol/methylene chloride. Impure fractions were chromatographed through silica gel eluted with 500 ml of 1% methanol/methylene chloride, 500 ml of 1.5% methanol/methylene chloride and 500 ml of 2% methanol/methylene chloride. 7.49 g (0.00923 mol) (74% by weight yield) of title compound was obtained.

The 5-methylsulfamoylindole used above was prepared as follows:

To 213 ml (3.21 mol) of ice-cold chlorosulfonic acid was added 100 g (0.680 mol) of N-formylindoline portionwise over 20 minutes. The reaction mixture was heated to 65° C. in an oil bath for 20 minutes while stirred mechanically. Then the solution was allowed to cool to room temperature. The solution was cautiously added to 2 liters of ice and filtered by suction filtration. The tan solid was washed with water and allowed to air dry to give 62.67 g (38% by weight yield) of 5-chlorosulfonyl-N-formylindoline.

To a solution of 31.07 g (0.126 mol) of N-formyl-5-chlorosulfonylindoline in 400 ml of ice-cold methylene chloride was added 37 ml (0.252 mol) of triethylamine and 30 ml (0.252 mol) of 40% aqueous methylamine solution, portionwise over twenty minutes. The mixture was allowed to warm to room temperature and then heated to reflux in an oil bath for one hour while stirred mechanically. Thin layer chromatography with chloroform showed the reaction was complete. The aqueous layer was removed. The methylene chloride layer was washed with water and dried over sodium sulfate. The solution was concentrated under reduced pressure and the residue allowed to air dry to give 23.74 g (0.0988 mol) (75% by weight yield) of 5-methylsulfamoyl-N-formylindoline.

To a stirred solution of 23.42 g (0.0975 mol) of 5-methylsulfamoyl-N-formylindoline in 500 ml of methanol was added 40 ml of concentrated hydrochloric acid. The solution was heated to reflux for one hour. Thin layer chromatography in chloroform showed the reaction was complete. The solution was allowed to cool, and then the methanol was removed under reduced pressure. The aqueous slurry remaining was dissolved ice water and neutralized by the addition of sodium hydroxide solution. The precipitate was extracted with methylene chloride, washed with water and saturated aqueous sodium chloride solution. The solution was dried over sodium sulfate and then concentrated under reduced pressure. The residue was allowed to air dry to give 17.02 g (0.08 mol) (82% by weight yield) of 5-methylsulfamoylindoline.

To a stirred solution of 12.87 g (0.0605 mol) of 5-methylsulfamoylindoline in 200 ml dioxane was added 15.11 g (0.0666 mol) of 2,3-dichloro-5,6-dicyano-1,4-benzoquinone. The mixture was heated to 75° C. in an oil bath for 2 hours. Thin layer chromatography in 3/1 hexane/acetone showed the reaction was complete. The solution was allowed to cool, filtered through Celite and concentrated under reduced pressure. The black residue was chromatographed through silica gel eluted with 2.5% methanol in methylene chloride. Thin layer chromatography showed a mixture of compounds. The residue was then chromatographed through a column of silica gel eluted with a 3/1 hexane/acetone. A purple compound was found to be inseparable from the 5-methylsulfamoylindole product. 4.42 g (0.021 mol) (35% by weight yield) of purple solid was obtained.

The compound of Example 1 also was synthesized using the foregoing procedure by reacting 6-methylsulfamoylindole with the naphthaldehydic acid.

EXAMPLE 3

3-(7-n-hexadecylsulfonamidoindol-3-yl)-3-(5-dimethylsulfamoylindol-3-yl)naphthalide having the formula

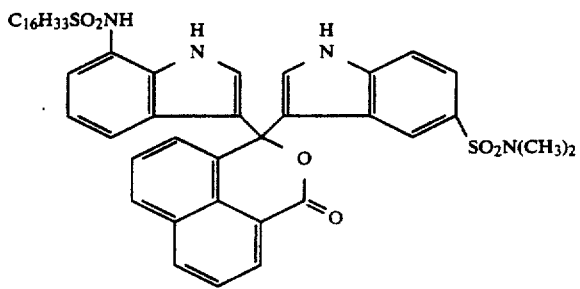

was prepared according to the procedure given in Example 2 except that the sulfamoylindole reacted with the oxidized naphthalidyl-indole intermediate was 5-dimethylsulfamoylindole. This indole was prepared in the same manner as 5-methylsulfamoylindole using dimethylamine.

EXAMPLE 4

3-(7-methylsulfonamidoindol-3-yl)-3-(5-n-hexadecylsulfamoylindol-3-yl)naphthalide having the formula

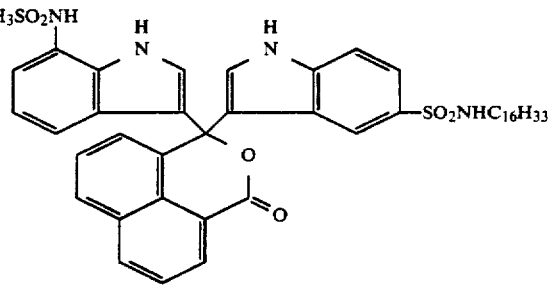

was prepared according to the procedure given in Example 2 above except that 5-n-hexadecylsulfamoylindole was reacted with an oxidized naphthalidyl-indole intermediate synthesized from 7-methylsulfonamidoindole.

EXAMPLE 5

3-(7-hexadecylsulfonamidoindole-3-yl)-3-(5-bromo-6-methylsulfamoylindole-3-yl)naphthalide having the formula

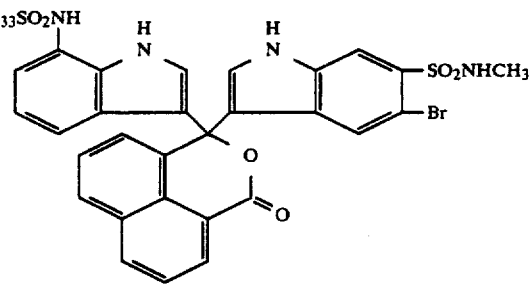

was prepared according to the procedure given in Example 2 except that the sulfamoylindole intermediate employed was 5-bromo-6-methylsulfamoylindole.

As noted above, the present invention is particularly adapted for facilitating processing outside of a camera of diffusion transfer units which are maintained as a permanent integral laminate after processing, the final transfer image being viewed through one face of the laminate. In such film units a light-reflecting layer is disposed between the developed photosensitive layers and the layer carrying the transfer dye image. These essential layers preferably are confined between a pair of dimensionally stable outer supports, at least one of which is transparent to permit viewing of the transfer dye image by reflection against the background provided by the reflecting layer.

Image dye-providing materials which may be employed generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise distribution as a function of development. These materials may be complete dyes or dye intermediates, e.g., color couplers. The requisite differential in mobility or solubility may, for example, be obtained by a chemical action such as a redox reaction or a coupling reaction.

As examples of initially soluble or diffusible materials and their application in color diffusion transfer processes, mention may be made of those disclosed, for example, in U.S. Pat. Nos. 2,968,554; 2,983,606; 3,087,817; 3,185,567; 3,230,082; 3,345,163; and 3,443,943. As examples of initially non-diffusible materials and their use use in color transfer systems, mention may be made of the materials and systems disclosed in U.S. Pat. Nos. 3,185,567; 3,443,939; 3,443,940; 3,227,550; 3,227,552 and 4,076,529. Both types of image dye-providing substances and film units useful therewith also are discussed in the aforementioned U.S. Pat. No. 3,647,437 to which reference may be made.

A particularly useful system for forming color images by diffusion transfer is that described in U.S. Pat. No. 2,983,606, employing dye developers (dyes which are also silver halide developing agents) as the image dye-providing materials. In such systems, a photosensitive element comprising at least one silver halide layer having a dye developer associated therewith (in the same or in an adjacent layer) is developed by applying an aqueous alkaline processing composition. Development of exposed silver halide results in oxidation of the dye developer to provide an oxidation product which is appreciably less diffusible than the unreacted dye developer, thereby providing an imagewise distribution of diffusible dye developer in terms of unexposed areas of the silver halide layer, which imagewise distribution is then tranferred, at least in part, by diffusion, to a dyeable stratum to impart thereto a positive dye transfer image.

In such color diffusion transfer systems, color transfer images are obtained by exposing a photosensitive element, sometimes referred to as a "negative component", comprising at least a light-sensitive layer, e.g., a gelatino silver halide emulsion layer, having an image dye-providing material associated therewith in the same or in an adjacent layer, to form a developable image; developing this exposed element with a processing composition to form an imagewise distribution of a diffusible image dye-providing material; and transferring this imagewise distribution, at least in part, by diffusion, to a superposed image-receiving layer, sometimes referred to as a "positive component", comprising at least a dyeable stratum to provide a color transfer image. The negative and positive components initially may be carried on separate supports which are brought together during processing and thereafter retained together as the final integral negative-positive reflection print, or they may initially comprise a unitary structure, e.g., integral negative-positive film units of the type described in aforementioned U.S. Pat. No. 3,415,644 wherein the negative and positive components are physically retained together in superposed relationship prior to, during and after image formation. (Procedures for forming such film units wherein the positive and negative components are temporarily laminated together prior to exposure are described, for example, in U.S. Pat. No. 3,652,281 to Albert J. Bachelder and Frederick J. Binda and in U.S. Pat. No. 3,652,282 to Edwin H. Land, both issued Mar. 28, 1972.) In either instance, the positive component is not removed from the negative component for viewing purposes. These components may be laminated together or otherwise secured together in physical juxtaposition.

Film units intended to provide multicolor images comprise two or more selectively sensitized silver halide layers each having associated therewith an appropriate image dye-providing material providing an image dye having spectral absorption characteristics substantially complementary to the light by which the associated silver halide is exposed. The most commonly employed negative components for forming multicolor images are of the tripack structure and contain blue-, green- and red-sensitive silver halide layers each having associated therewith in the same or in a contiguous layer a yellow, a magenta and a cyan image dye-providing material respectively. Interlayers or spacer layers may be provided between the respective silver halide layers and associated image dye-providing materials or between other layers. Indeed, a light-reflecting spacer layer disposed between a silver halide layer and the associated layer of image dye-providing material may be used to increase effective film speed as a result of the reflection of light back to the silver halide. Particularly suitable light-reflecting spacer layers comprise a light-reflecting pigment dispersed with inert polymeric particles which are substantially non-swelling in alkali and substantially non-film-forming. Such layers form the subject matter of published European Patent Application No. 0066341 published Dec. 8, 1982.

In addition to the aforementioned layers, such film units further include means for providing a reflecting layer between the dyeable stratum and the negative component in order to mask effectively the silver image or images formed as a function of development of the silver halide layer or layers and also to mask image dye-providing material which is not transferred, thereby providing a background, preferably white, for viewing the color image formed in the dyeable stratum, without separation, by reflected light. Preferably, this reflecting layer is provided by including the reflecting agent in the processing composition. The dye transfer image is then viewable against the reflecting layer through a dimensionally stable protective layer or support. As noted above, most preferably another dimensionally stable layer or support is positioned on the opposed surface of the essential layers so that the aforementioned essential layers are between a pair of dimensionally stable layers or support members, one of which is transparent to permit viewing therethrough of the color transfer image. A rupturable container of known description contains the requisite processing composition and is adapted upon application of pressure to release its contents for development of the exposed film unit, e.g., by distributing the processing composition in a substantially uniform layer between the negative and positive components.

The dye developers (or other image dye-providing substances) are preferably selected for their ability to provide colors that are useful in carrying out subtractive color photography, that is, the previously mentioned cyan, magneta and yellow. They may be incorporated in the respective silver halide emulsion or, in the preferred embodiment, in a separate layer behind the respective silver halide emulsion. Thus a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide development function is a hydroquinonyl group. Other suitable developing functions include orthodihydroxyphenyl and ortho- and para-amino substituted hydroxyphenyl groups. In general, the development function includes a benzenoid developing function, that is, an aromatic developing group which forms quinonoid or quinone substances when oxidized.

The image-receiving layer may comprise any of the materials known in the art, such as polyvinyl alcohol, gelatin, etc., preferably containing a mordant for the transferred image dye(s). If the color of the transferred image dye(s) is affected by changes in pH, the pH of the image layer may be adjusted to provide a pH affording the desired color.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. These polymeric acids may be polymers which contain acid groups, e.g., carboxylic acid and sulfonic acid groups, which are capable of forming salts with alkali; or potentially acid-yielding groups such as anhydrides or lactones. Preferably the acid polymer contains free carboxyl groups. Alternatively, the acid-reacting reagent may be in a layer adjacent the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be used in association with the polymeric acid layer to control or "time" the pH reduction so that it is not premature and interfere with the development process. Suitable spacer or "timing" layers useful for this purpose are described with particularity in U.S. Pat. Nos. 3,362,819; 3,419,389; 3,421,893; 3,455,686; and 3,575,701.

As is now well known and illustrated, for example, in the previously cited patents, the liquid processing composition referred to for effecting multicolor diffusion transfer processes comprises at least an aqueous solution of an alkaline material and possesses a pH of at least 12. Preferably, the alkaline material employed in the subject invention, is an alkali metal hydroxide.

The processing composition also preferably includes a viscosity-imparting reagent constituting a film-forming material of the type which, when the composition is spread and dried, forms a relatively firm and relatively stable film. This reagent may be a cellulosic polymer, for example, hydroxyethyl cellulose or sodium carboxymethyl cellulose; an oxime polymer, for example, polydiacetone acrylamide oxime; or other alkali-stable high molecular weight polymer. The viscosity-imparting reagent is preferably contained in the processing composition in such suitable quantities as to impart to the composition a viscosity in excess of 100 cps. at a temperature of approximately 24° C. and preferably in the order of 100,000 cps. to 200,000 cps. at that temperature.

As mentioned previously, a light-absorbing pH-sensitive optical filter agent which absorbs in the longer wavelength range of the visible spectrum, usually, a carboxynaphthol phthalein is used in combination with the subject indole phthaleins to provide further protection throughout the visible spectrum. As used herein, the term "carboxynaphthol phthalein" is intended to include both 3,3-di(4'-hydroxy-1'-naphthyl)-phthalides and 3,3-di(4'-hydroxy-1'-naphthyl)-naphthalides wherein at least one of said 3,3-substituents is a 3'-carboxy-4'-hydroxy-1'-naphthyl moiety such as the phthaleins disclosed in aforementioned U.S. Pat. No. 3,702,245.

The pH-sensitive phthalein dye(s) employed as the light-absorbing optical filter agents preferably are initially contained in the processing composition in their colored form together with the light-reflecting material, for example, titanium dioxide. The concentration of phthalein dye is selected to provide the optical transmission density required, in combination with the other layers intermediate the silver halide emulsion layer(s) and the incident radiation, to prevent nonimagewise exposure, i.e., fogging by incident actinic light during performance of the particular photographic process. The transmission density and the concentration of phthalein dye necessary to provide the requisite protection from incident light may be readily determined for any photographic process by routine experimentation, as a function of film speed or sensitivity, thickness of the opacification layer, processing time, anticipated incident light intensity, etc., as described in said U.S. Pat. No. 3,647,437. It will be recognized that a particular transmission density may not be required for all portions of the spectrum, lesser density being sufficient in wavelength regions corresponding to lesser sensitivities of the particular photosensitive material. As indicated above, it will be recognized that a mixture of phthalein dyes may be used to obtain absorption in all critical areas of the visible and near-visible by which the silver halide emulsions being used are exposable.

Where the light-absorbing phthalein optical filter agent is present in the processing composition, it is advantageous to utilize an image-receiving component having a surface layer adapted to decolorize the optical filter agent adjacent the interface between said component and the layer of processing composition. Suitable decolorizing layers are described in U.S. Pat. No. 4,298,674 of Edwin H. Land, Leon D. Cerankowski and Neil C. Mattucci, in U.S. Pat. No. 4,294,907 of Irena Bronstein-Bonte, Edward P. Lindholm and Lloyd D. Taylor and in U.S. Pat. No. 4,367,277 of Charles K. Chiklis and Neil C. Mattucci.

To further illustrate the present invention, the transmission densities of each of the compounds of Examples 1, 2 and 3 at a concentration of $1 \times 10^{-5}$ M in a solution of a 1:4 mixture of ethanol in 10% aqueous sodium hydroxide were measured spectrophotometrically over the wavelength range of 340 nm to 700 nm. The resulting curves designated Curves 1, 2 and 3 are shown in FIG. 1. As a comparison, the transmission density of 3-(7-carboxyindol-3-yl)-3-(7-n-hexadecylsulfonamidoindol-3-yl)naphthalide was measured in the same manner and at the same concentration in a 1:4 ethanol/10% aqueous sodium hydroxide solution. The resulting curve is designated Curve C in FIG. 1.

As can be seen from reference to FIG. 1, the indole phthaleins of the present invention as compared to the 7-carboxy/7-sulfonamido indole phthalein absorb more strongly in the green region of the visible spectrum. The $\lambda_{max}$ and Epsilon measured at the $\lambda_{max}$ were 533 (32,200), 533 (30,860) and 530 (31,100) for the compounds of Examples 1, 2 and 3, respectively, as compared to 467 (15,300) for the 7-carboxy-7-sulfonamido compound.

The transmission densities measured for the compounds of Examples 4 and 5 under the same conditions had a $\lambda_{max}$ and Epsilon at the $\lambda_{max}$ of 532 (30,020) and 532 (34,450), respectively. When measured in the same manner using 5% instead of 10% aqueous sodium hydroxide, the $\lambda_{max}$ and Epsilon for the compounds of Examples 1 through 5 were 518 (25,150), 512 (25,250), 526 (26,200), 525 (22,750) and 525 (30,470), respectively, whereas the $\lambda_{max}$ and Epsilon for the 7-carboxy/7-sulfonamido compound was 466–467 (12,600).

Figure 2:
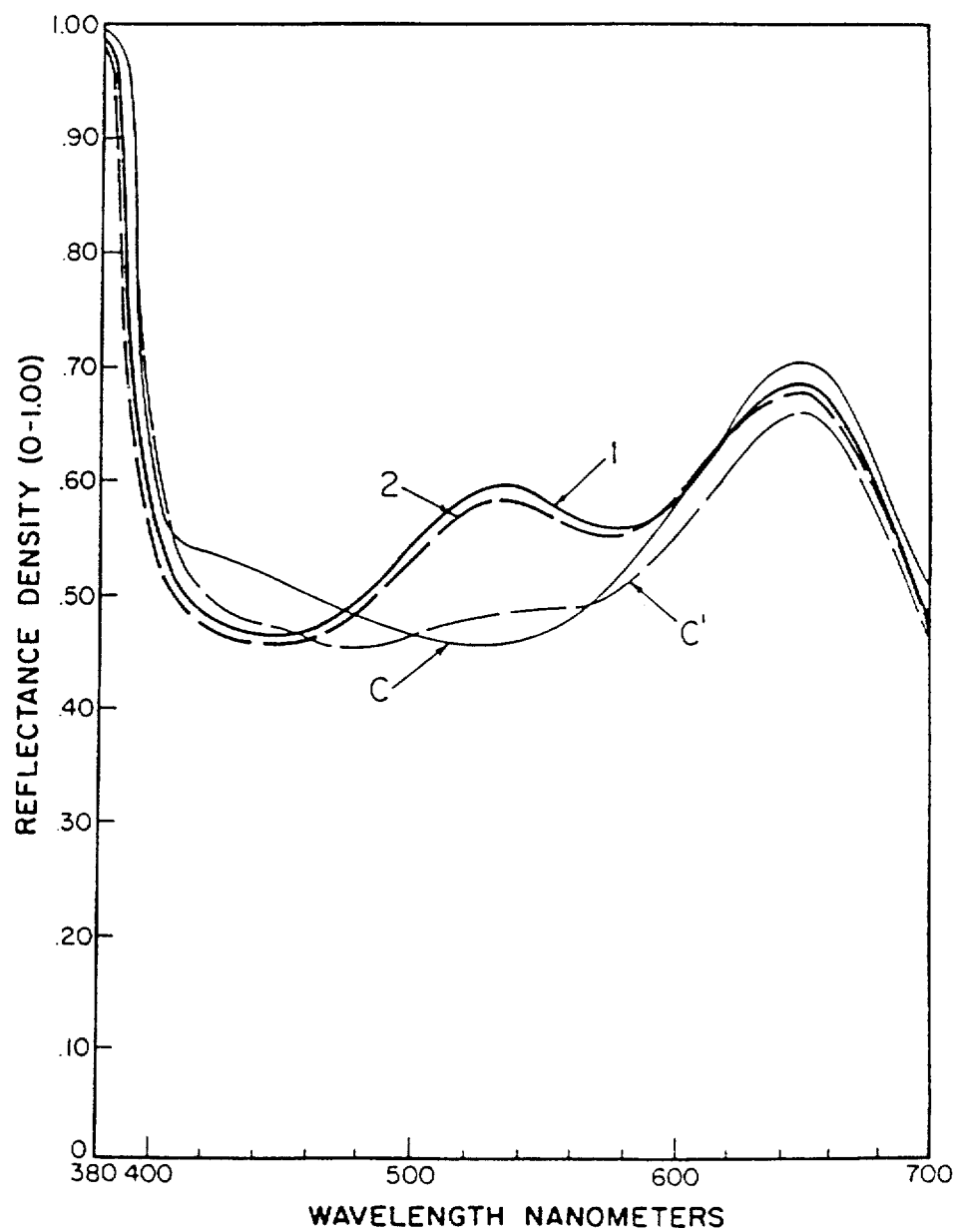
FIGS. 2 and 3 are graphic illustrations showing the reflectance densities of pigmented processing compositions over the wavelength range of 380 nm to 700 nm wherein the compositions are the same except for the indole phthalein optical filter agent. Curves 1, 2 and 3 represent the reflectance densities obtained using optical filter agents of the present invention, namely, the indole phthaleins of Examples 1, 2 and 3, respectively. Curves C and C' represent the reflectance densities obtained using a 7-carboxy/7-sulfonamido indole phthalein and a 7-sulfonamido/7-sulfamoyl indole phthalein, respectively.
Figure 3:
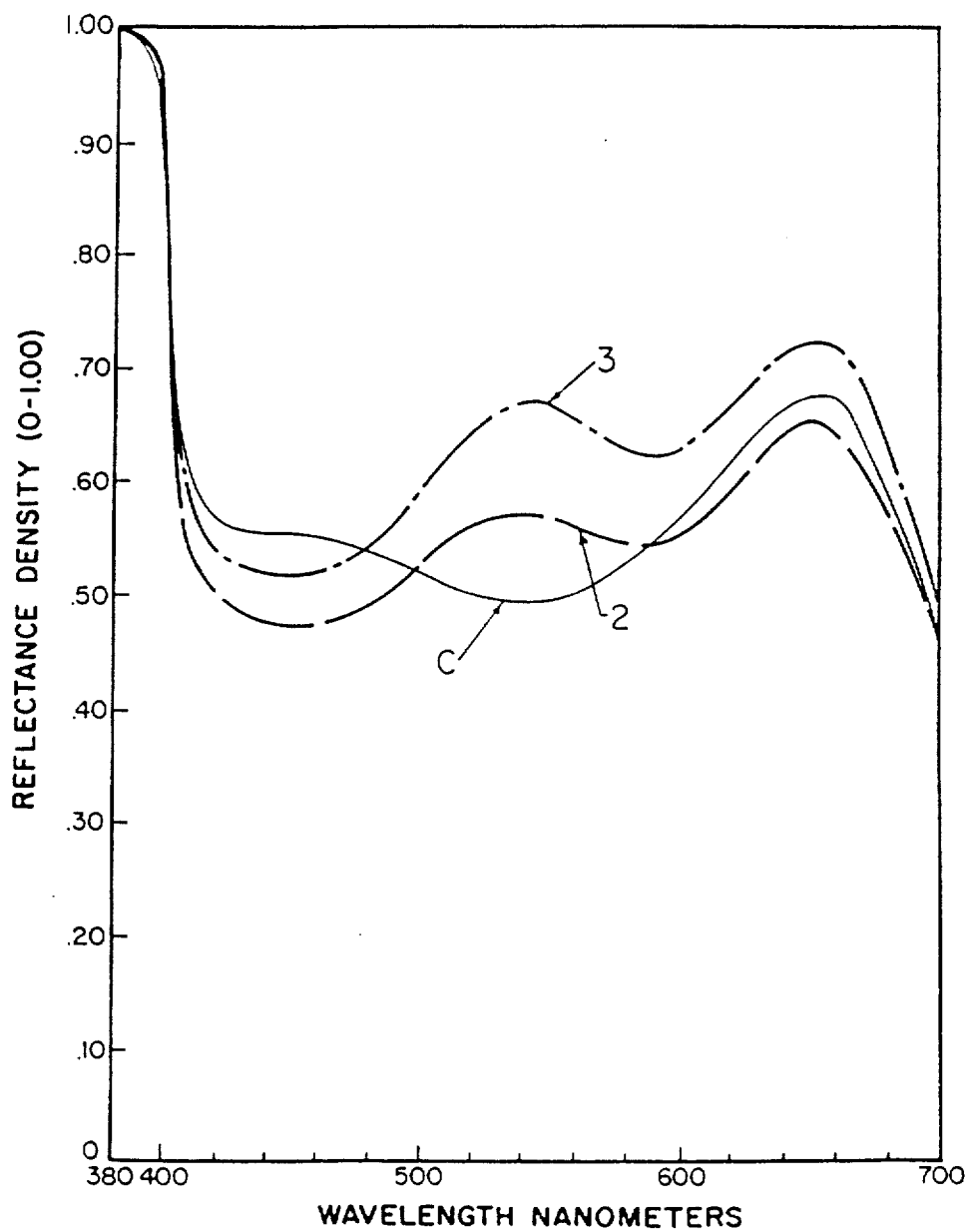

The increased protection in the green region provided by the subject indole phthaleins is further illustrated in FIGS. 2 and 3 which represent the reflectance spectra for pigmented processing composition layers containing the same ingredients except for the indole phthalein optical filter agent used as the shorter wavelength absorber. Curves 1 and 2 in FIG. 2 represent pigmented processing composition layers containing the compounds of Examples 1 and 2, respectively, and Curves C and C' represent pigmented processing composition layers containing 3-(7-carboxyindol-3-yl)-3-(7-n-hexadecylsulfonamidoindol-3-yl)naphthalide and 3-(7-n-hexadecylsulfonamidoindol-3-yl)-3-(7-methylsulfamoylindol-3-yl)naphthalide, respectively. In FIG. 3, Curves 2 and 3 represent pigmented processing composition layers containing the compounds of Examples 2 and 3, respectively, and Curve C represents a pigmented processing composition layer containing 3-(7-carboxyindol-3-yl)-3-(7-n-hexadecylsulfonamidoindol-3-yl)naphthalide. Besides the respective indole phthalein shorter wevelength absorbers, the aqueous alkaline processing composition comprised a viscous aqueous solution of an alkali metal hydroxide containing titanium dioxide as the light-reflecting pigment and the carboxynaphthol phthalein of the following formula as the optical filter agent for absorbing in the longer wavelength range of the visible spectrum.

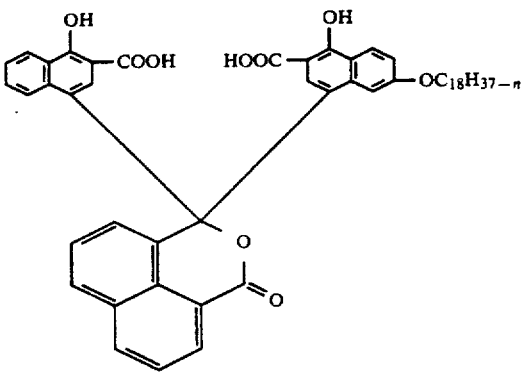

3-(3'-carboxy-4'hydroxy-1'-naphthyl)-3-(3''-carboxy-4''-hydroxy-7''-octadecyloxy-1''-naphthyl)naphthalide The respective processing compositions were spread between two transparent sheets of polyethylene terephthalate in a layer approximately 0.0028 inch thick and the reflectance density of each layer was measured over the wavelength range of 380 to 700 nm.

It will be apparent from a comparison of Curves 1 and 2 with C and C' in FIG. 2 and from a comparison of Curves 2 and 3 with Curve C in FIG. 3 that the pigmented processing composition layers containing the indole phthaleins of the present invention afford more effective protection in the green region of the visible spectrum as evidenced by the substantial increase in reflectance density above 500 nm, particularly in the 520 to 550 nm range.

It will be understood that this invention is applicable to a wide variety of photographic processes employing any of various image-providing materials and that the transfer image may be in silver or in dye. Since such processes are now well known, it is not necessary to describe them in detail.

It will be understood that in any of these photographic systems, the transfer image may be positive or negative with respect to the photographic subject matter as a function of the particular image-forming system and that the silver halide emulsion may be negative-working or positive-working. Likewise, the image-receiving layer or other layers of the negative and positive components may vary as appropriate for a given process.

Since certain changes may be made in the above subject matter without departing from the scope of the invention herein involved, it is intended that all matter contained in the above description or shown in the accompanying drawings shall be interpreted as illustrative and not in a limiting sense.

What is claimed is:

1. In a photographic process for forming a diffusion transfer image viewable as a reflection print which includes the steps of applying a layer of aqueous alkaline processing composition comprising a light-reflecting pigment and at least one light-absorbing pH-sensitive optical filter agent between a negative component comprising an exposed silver halide emulsion carried on a support and a positive component comprising an image-receiving layer carried on a transparent support; said layer of processing composition being effective to develop said exposed silver halide emulsion and to form a visible image in said image-receiving layer and being effective to prevent transmission of light actinic to said silver halide emulsion during development thereof; and after a predetermined time, reducing the pH of said processing composition layer to a pH effective to decolorize said pH-sensitive optical filter agent; said pH reduction being effected by an acid-reacting layer disposed in at least one of said negative and positive components;

the improvement which comprises applying as said processing composition layer, an aqueous alkaline solution comprising a light-reflecting pigment and as at least one said light-absorbing pH-sensitive optical filter agent, a pH-sensitive indole phthalein of the formula

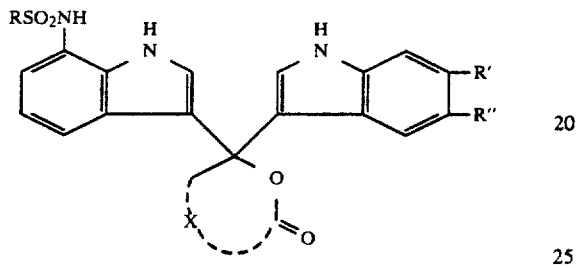

wherein R is selected from alkyl, aryl, aralkyl and alkaryl, R' and R" each are selected from hydrogen, halo and —$SO_2NR^1R^2$ provided one of said R' and R" is said —$SO_2NR^1R^2$, $R^1$ and $R^2$ each are selected from hydrogen, alkyl, aryl, aralkyl and alkaryl, and X represents the carbon atoms necessary to complete phthalide or naphthalide.

2. A photographic process as defined in claim 1 wherein said X completes naphthalide.

3. A photographic process as defined in claim 2 wherein said R is alkyl.

4. A photographic process as defined in claim 3 wherein said $R^1$ is hydrogen and said $R^2$ is alkyl.

5. A photographic process as defined in claim 3 wherein said $R^1$ and $R^2$ each are alkyl.

6. A photographic process as defined in claim 1 wherein said processing composition additionally includes a viscosity-imparting reagent.

7. A photographic process as defined in claim 1 wherein said light-reflecting pigment is titanium dioxide.

8. A photographic process as defined in claim 1 wherein said processing composition includes a light-absorbing, pH-sensitive carboxynaphthol phthalein optical filter agent.

9. In a photographic film unit adapted for forming a transfer image viewable as a reflection print including a negative component comprising a photosensitive silver halide emulsion carried on a support; a positive component comprising an image-receiving layer carried on a transparent support; an acid-reacting layer disposed in at least one of said negative and positive components; and an aqueous alkaline processing composition comprising a light-reflecting pigment and at least one light-absorbing, pH sensitive optical filter agent releasably contained in a rupturable container positioned to release said composition for distribution between said negative and said positive components, the combination of said light-reflecting pigment and said optical filter agent being effective to prevent further exposure of said photosensitive emulsion during processing in the presence of radiation actinic to said emulsion and said light-reflecting pigment providing a layer after development which is effective to mask said photosensitive layer and provide a background for viewing the transfer image by reflected light;

the improvement which comprises employing as said processing composition, an aqueous alkaline solution comprising a light-reflecting pigment and as at least one said light-absorbing pH-sensitive optical filter agent, a pH-sensitive indole phthalein of the formula

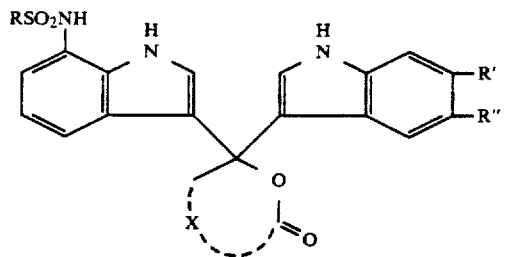

wherein R is selected from alkyl, aryl, aralkyl and alkaryl, R' and R" each are selected from hydrogen, halo and —$SO_2NR^1R^2$ provided one of said R' and R" is said —$SO_2NR^1R^2$, $R^1$ and $R^2$ each are selected from hydrogen, alkyl, aryl, aralkyl and alkaryl, and X represents the carbon atoms necessary to complete phthalide or naphthalide.

10. A photographic product as defined in claim 9 wherein said X completes naphthalide.

11. A photographic product as defined in claim 10 wherein said R is alkyl.

12. A photographic product as defined in claim 11 wherein said $R^1$ is hydrogen and said $R^2$ is alkyl.

13. A photographic product as defined in claim 11 wherein said $R^1$ and $R^2$ each are alkyl.

14. A photographic product as defined in claim 9 wherein said processing composition additionally includes a viscosity-imparting reagent.

15. A photographic product as defined in claim 9 wherein said light-reflecting pigment is titanium dioxide.

16. A photographic product as defined in claim 9 wherein said processing composition includes a light-absorbing, pH-sensitive carboxynaphthol phthalein optical filter agent.

17. A rupturable container for use in diffusion transfer film units adapted to provide transfer images viewable by reflected light, said rupturable container releasably holding an aqueous alkaline processing composition comprising an aqueous solution of alkali metal hydroxide, a light-reflecting pigment and at least one light-absorbing, pH-sensitive optical filter agent, at least one said optical filter agent being a pH-sensitive indole phthalein of the formula

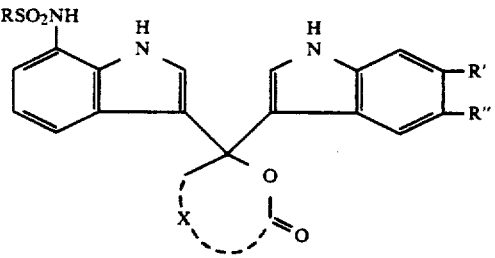

wherein R is selected from alkyl, aryl, aralkyl and alkaryl, R' and R" each are selected from hydrogen, halo and —SO$_2$NR$^1$R$^2$ provided one of said R' and R" is said —SO$_2$NR$^1$R$^2$, R$^1$ and R$^2$ each are selected from hydrogen, alkyl, aryl, aralkyl and alkaryl, and X represents the carbon atoms necessary to complete phthalide or naphthalide.

18. A rupturable container releasably holding an aqueous alkaline processing composition as defined in claim 17 wherein said X completes naphthalide.

19. A rupturable container releasably holding an aqueous alkaline processing composition as defined in claim 17 wherein said R is alkyl.

20. A rupturable container releasably holding an aqueous alkaline processing composition as defined in claim 19 wherein said R$^1$ is hydrogen and said R$^2$ is alkyl.

21. A rupturable container releasably holding an aqueous alkaline processing composition as defined in claim 19 wherein said R$^1$ and R$^2$ each are alkyl.

22. A rupturable container releasably holding an aqueous alkaline processing composition as defined in claim 17 wherein said processing composition additionally includes a viscosity-imparting reagent.

23. A rupturable container releasably holding an aqueous alkaline processing composition as defined in claim 17 wherein said light-reflecting pigment is titanium dioxide.

24. A rupturable container releasably holding an aqueous alkaline processing composition as defined in claim 17 wherein said processing composition includes a light-absorbing, pH-sensitive carboxynaphthol phthalein optical filter agent.

25. A compound having the formula

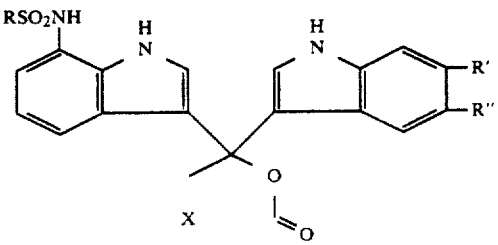

wherein R' and R" each are selected from hydrogen, halo and —SO$_2$NR$^1$R$^2$ provided one of said R' and R" is said —SO$_2$NR$^1$R$^2$, R$^1$ and R$^2$ each are selected from hydrogen, alkyl, aryl, aralkyl and alkaryl, R is selected from alkyl, aryl, aralkyl and alkaryl and X represents the carbon atoms necessary to complete phthalide or naphthalide.

26. A compound as defined in claim 25 wherein said X completes naphthalide.

27. A compound as defined in claim 26 wherein said R is alkyl.

28. A compound as defined in claim 27 wherein said R$^1$ is hydrogen and said R$^2$ is alkyl.

29. A compound as defined in claim 27 wherein said R$^1$ and R$^2$ each are alkyl.

* * * * *